United States Patent
Palazzotto et al.

(10) Patent No.: US 9,279,792 B2
(45) Date of Patent: Mar. 8, 2016

(54) METHOD OF USING AN ABSORPTIVE SENSOR ELEMENT

(75) Inventors: Michael C. Palazzotto, Woodbury, MN (US); Stefan H. Gryska, Woodbury, MN (US); Myungchan Kang, Woodbury, MN (US); Michael S. Wendland, North St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 29 days.

(21) Appl. No.: 14/007,106

(22) PCT Filed: Mar. 27, 2012

(86) PCT No.: PCT/US2012/030676
§ 371 (c)(1),
(2), (4) Date: Sep. 24, 2013

(87) PCT Pub. No.: WO2012/141883
PCT Pub. Date: Oct. 18, 2012

(65) Prior Publication Data
US 2015/0109003 A1    Apr. 23, 2015

Related U.S. Application Data

(60) Provisional application No. 61/475,011, filed on Apr. 13, 2011.

(51) Int. Cl.
*G01R 27/08* (2006.01)
*G01N 33/00* (2006.01)
(Continued)

(52) U.S. Cl.
CPC ............... *G01N 33/00* (2013.01); *G01N 21/55* (2013.01); *G01N 21/783* (2013.01); *G01N 27/22* (2013.01); *G01N 27/227* (2013.01); *G01N 33/0047* (2013.01)

(58) Field of Classification Search
CPC ....... G01N 33/00; G01N 27/22; G01N 21/55; G01N 27/227; G01N 21/783; G01N 33/0047
USPC .................... 356/402; 324/658–690
See application file for complete search history.

(56) References Cited

U.S. PATENT DOCUMENTS 4,638,443 A    1/1987    Kaneyasu et al.
4,703,646 A    11/1987   Muller et al.
(Continued)

FOREIGN PATENT DOCUMENTS

DE    10041921    3/2002
EP    1030174     8/2000
(Continued)

OTHER PUBLICATIONS

Budd, "Polymers of intrinsic microporosity (PIMs): robust, solution-processable, organic nanoporous materials", Chemical Communications, 2004, pp. 230-231.
(Continued)

*Primary Examiner* — Jermele M Hollington
*Assistant Examiner* — Farhana Hoque
(74) *Attorney, Agent, or Firm* — Yufeng Dong

(57) ABSTRACT

A method of using an absorptive sensor element includes: providing the absorptive sensor element, heating the absorptive sensor element to a temperature in a range of from 30° C. to 100° C., exposing the absorptive sensor element to an analyte vapor, and measuring a capacitance-related property of the absorptive sensor element and/or a spectral feature upon reflection of incident light. The absorptive sensor element comprises: a substrate, a first member disposed on the substrate, a second member, and a detection layer comprising a polymer of intrinsic microporosity disposed between and contacting the first member and the second member.

8 Claims, 1 Drawing Sheet

(51) Int. Cl.
*G01N 21/78* (2006.01)
*G01N 27/22* (2006.01)
*G01N 21/55* (2014.01)

(56) References Cited

U.S. PATENT DOCUMENTS

| | | | |
|---|---|---|---|
| 4,975,249 | A | 12/1990 | Elliott |
| 5,269,175 | A | 12/1993 | Chmiel et al. |
| 5,296,819 | A | 3/1994 | Kuroiwa et al. |
| 5,511,418 | A | 4/1996 | Antikainen et al. |
| 5,709,792 | A | 1/1998 | Zdanevitch et al. |
| 5,777,206 | A | 7/1998 | Zuchner et al. |
| 5,788,833 | A * | 8/1998 | Lewis et al. ......... 205/787 |
| 5,987,963 | A | 11/1999 | Stormbom |
| 6,165,347 | A | 12/2000 | Warburton |
| 6,320,388 | B1 | 11/2001 | Sun et al. |
| 6,338,266 | B1 | 1/2002 | Warburton |
| 6,356,087 | B1 | 3/2002 | Wallrafen |
| 6,435,003 | B1 | 8/2002 | Warburton |
| 6,455,319 | B1 | 9/2002 | Lewis |
| 6,471,838 | B1 | 10/2002 | Igel |
| 6,571,603 | B1 | 6/2003 | Doleman |
| 6,596,236 | B2 | 7/2003 | DiMeo |
| 6,640,626 | B2 | 11/2003 | Saikalis |
| 6,691,582 | B1 | 2/2004 | Nawa |
| 6,787,047 | B1 | 9/2004 | Hahn |
| 6,815,211 | B1 | 11/2004 | Blazewicz |
| 6,895,338 | B2 | 5/2005 | Hsiung |
| 6,921,883 | B2 | 7/2005 | Kato |
| 7,160,690 | B2 | 1/2007 | Orser |
| 7,200,495 | B2 | 4/2007 | Desai |
| 7,228,725 | B2 | 6/2007 | Salter |
| 7,323,343 | B2 | 1/2008 | Cox |
| 7,449,146 | B2 | 11/2008 | Rakow |
| 7,556,774 | B2 | 7/2009 | Rakow |
| 7,680,607 | B1 | 3/2010 | Smulko |
| 7,767,143 | B2 | 8/2010 | Wendland |
| 7,816,681 | B2 | 10/2010 | Moon |
| 7,906,233 | B2 | 3/2011 | Wang |
| 2002/0098119 | A1 | 7/2002 | Goodman |
| 2002/0142478 | A1 | 10/2002 | Wado |
| 2003/0020494 | A1 | 1/2003 | Desmier |
| 2003/0109056 | A1 | 6/2003 | Vossmeyer |
| 2003/0166296 | A1 | 9/2003 | Morrison |
| 2003/0235817 | A1 | 12/2003 | Bartkowiak |
| 2004/0060818 | A1 * | 4/2004 | Feldman et al. ......... 204/403.01 |
| 2005/0014179 | A1 | 1/2005 | Karlsson |
| 2005/0045493 | A1 | 3/2005 | Mahurin |
| 2005/0100475 | A1 | 5/2005 | Centanni |
| 2005/0148003 | A1 | 7/2005 | Keith |
| 2006/0078960 | A1 | 4/2006 | Hunter |
| 2006/0246273 | A1 | 11/2006 | McKeown |
| 2006/0249402 | A1 | 11/2006 | Snow |
| 2007/0060811 | A1 | 3/2007 | Roberts |
| 2007/0118027 | A1 | 5/2007 | Baker |
| 2007/0140907 | A1 | 6/2007 | Rakow |
| 2007/0141580 | A1 | 6/2007 | David |
| 2007/0177130 | A1 | 8/2007 | MacIntyre |
| 2007/0190637 | A1 | 8/2007 | Samsoondar |
| 2007/0299617 | A1 | 12/2007 | Willis |
| 2008/0063575 | A1 | 3/2008 | Rakow |
| 2008/0086273 | A1 | 4/2008 | Shults |
| 2008/0137066 | A1 | 6/2008 | Weinstein |
| 2008/0270039 | A1 | 10/2008 | Dunn |
| 2008/0288182 | A1 | 11/2008 | Cline |
| 2008/0312859 | A1 | 12/2008 | Skyggebjerg |
| 2009/0018426 | A1 | 1/2009 | Markle |
| 2009/0076360 | A1 | 3/2009 | Brister |
| 2009/0112478 | A1 | 4/2009 | Mueller, Jr. |
| 2009/0126460 | A1 | 5/2009 | Gardner et al. |
| 2009/0192745 | A1 | 7/2009 | Kamath et al. |
| 2009/0283421 | A1 | 11/2009 | Farangis et al. |
| 2010/0189600 | A1 | 7/2010 | Hulteen et al. |
| 2010/0277740 | A1 * | 11/2010 | Hulteen et al. ....... G01N 21/274 356/445 |
| 2010/0325073 | A1 | 12/2010 | Haick |
| 2011/0031983 | A1 | 2/2011 | David et al. |
| 2011/0045601 | A1 | 2/2011 | Gryska et al. |
| 2013/0088244 | A1 | 4/2013 | Gryska et al. |
| 2013/0186177 | A1 | 7/2013 | Palazzotto |
| 2013/0229194 | A1 | 9/2013 | Palazzotto |

FOREIGN PATENT DOCUMENTS

| | | |
|---|---|---|
| EP | 2009432 | 12/2008 |
| JP | 6-281610 | 10/1994 |
| WO | WO 99-08105 | 2/1999 |
| WO | WO 99-29230 | 6/1999 |
| WO | WO 01-01121 | 1/2001 |
| WO | WO 01-81890 | 11/2001 |
| WO | WO 02-39103 | 5/2002 |
| WO | WO 03-029800 | 4/2003 |
| WO | WO 03-063699 | 8/2003 |
| WO | WO 2005-012397 | 2/2005 |
| WO | WO 2006-099518 | 9/2006 |
| WO | WO 2007-009268 | 1/2007 |
| WO | WO 2007-029033 | 3/2007 |
| WO | WO 2008-002743 | 1/2008 |
| WO | WO 2008-077745 | 7/2008 |
| WO | WO 2009-001065 | 12/2008 |
| WO | WO 2009-001070 | 12/2008 |
| WO | WO 2009-045733 | 4/2009 |
| WO | WO 2009-046011 | 4/2009 |
| WO | WO 2009-053981 | 4/2009 |
| WO | WO 2010-075333 | 7/2010 |
| WO | WO 2010-088088 | 8/2010 |
| WO | WO 2010-117599 | 10/2010 |
| WO | WO 2010-135413 | 11/2010 |
| WO | WO 2012-050686 | 4/2012 |
| WO | WO 2012-141883 | 10/2012 |
| WO | WO 2012-141894 | 10/2012 |
| WO | WO 2012-141925 | 10/2012 |
| WO | WO 2012-141958 | 10/2012 |
| WO | WO 2012-170248 | 12/2012 |
| WO | WO 2012-174099 | 12/2012 |
| WO | WO 2013-090188 | 6/2013 |

OTHER PUBLICATIONS

Budd, "Free volume and intrinsic microporosity in polymers", J. Mater. Chem., 2005, vol. 15, pp. 1977-1986.

Budd, "Solution-Processed, Organophilic Membrane Derived from a Polymer of Intrinsic Microporosity", Advanced Materials, Mar. 2004, vol. 16, No. 5, pp. 456-459.

Carta, "Novel Spirobisindanes for use as precursors to polymers of intrinsic microporosity", Organic Letters, 2008, vol. 10, No. 13, pp. 2641-2643.

Dai, "A capacitive humidity sensor integrated with micro heater and ring oscillator circuit fabricated by CMOS-MEMS technique", Sensors and Actuators B Chemical, 2007, vol. 122, pp. 375-380.

Endres, "A gas sensor system with dielectric and mass sensors", Sensors and Actuators B Chemical, Jan. 1992, vol. 6, No. 1-3, pp. 285-288.

Furjes, "Porous silicon-based humidity sensor with interdigital electrodes and internal heaters", Sensors and Actuators B Chemical, Oct. 2003, vol. 95, No. 1-3, pp. 140-144.

Ghanem, "High-Performance Membranes from Polyimides with Intrinsic Microporosity", Adv. Mater., Jul. 17, 2008, vol. 20, No. 14, pp. 2766-2771.

Ghanem, "Polymers of Intrinsic Microporosity Derived from Bis(phenaryl) Monomers", Macromolecules, 2008, vol. 41, No. 5, pp. 1640-1646.

Matsuguchi, "Capacitive-Type Humidity Sensors Using Polymerized Vinyl Carboxylate", J. Electrochemical Soc., Mar. 1994, vol. 141, No. 3, pp. 614-618.

(56) References Cited

OTHER PUBLICATIONS

McKeown, "Polymers of Intrinsic Microporosity (PIMs): Bridging the Void between Microporous and Polymeric Materials", Chem. Eur. J., 2005, vol. 11, No. 9, pp. 2610-2620.

Patel, "Chemicapacitive Microsensors for Volatile Organic Compound Detection", Sensors and Actuators B Chemical, Dec. 1, 2003, vol. 96, No. 3, pp. 541-553.

Smiths Detection, The Cyranose 320 E Nose User's Manual 11-6001, Edition 5, 2000, 102 pages.

International Search Report for PCT International Application No. PCT/US2012/030676, Mailed on Jun. 11, 2012, 4 pages.

Co-pending U.S. Appl. No. 14/007,144 entitled "Method of Using an Absorptive Sensor Element", Palazzotto et al., filed Sep. 24, 2013.

Co-pending U.S. Appl. No. 14/007,230, entitled "Method of Detecting Volatile Organic Compounds", Kang et al., filed Sep. 24, 2013.

Co-pending U.S. Appl. No. 14/110,047, entitled "Vapor Sensor Including Sensor Element with Integral Heating", Palazzotto et al., filed Oct. 4, 2013.

* cited by examiner

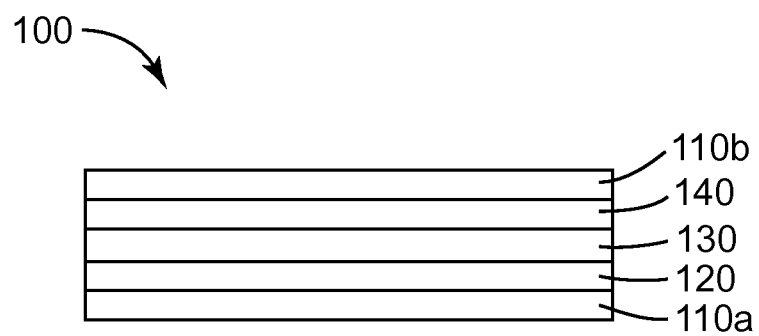

METHOD OF USING AN ABSORPTIVE SENSOR ELEMENT

FIELD

The present disclosure broadly relates to methods of sensing an analyte vapor.

BACKGROUND

The detection of volatile organic compounds (VOCs) is of potential importance in many applications due to environmental and safety concerns. Various methods for VOCs detection have been developed using photoionization, gravimetry, spectroscopy, and so forth. In many current commercialized VOCs detection technologies, VOCs cannot be identified. For example, the popular detection technology, Photo-Ionization Detection (PID), requires prior identification of any VOCs in order to obtain quantitative information. In order to identify VOCs, sophisticated and expensive equipment such as, for example, Gas Chromatography-Mass Spectrometry (GCMS) equipment is generally used. Despite miniaturization efforts, GCMS remains difficult and expensive to use in the field (e.g., in a manufacturing facility or shop).

Various absorptive capacitance sensors and optochemical sensors have been devised that include a dielectric microporous material such as, for example, a so-called-polymer of intrinsic microporosity (PIM) disposed between and contacting two layers, at least one of which is porous to analyte vapors (e.g., volatile organic compounds) that become absorbed by the dielectric microporous material. As used herein the term "absorb" refers to material becoming disposed within the dielectric microporous material, regardless of whether it is merely adsorbed to the pore walls, or dissolved into the bulk dielectric microporous material. These sensors detect changes in properties of the microporous material due to absorbed VOCs. For example, optochemical sensors detect changes in reflected light caused by a change in the index of refraction of the dielectric microporous material, and capacitance sensors detect changes in capacitance caused by a change in dielectric constant of the dielectric microporous material.

SUMMARY

In one aspect, the present disclosure provides a method of using an absorptive sensor element, the method comprising the steps:

a) providing the absorptive sensor element, wherein the absorptive sensor element comprises: a first member, a second member, and a detection layer comprising a polymer of intrinsic microporosity disposed between and contacting the first member and the second member;

b) heating the absorptive sensor element to a temperature in a range of from 30° C. to 100° C.;

c) exposing the absorptive sensor element to an analyte vapor, while the absorptive sensor element is at the elevated temperature; and d) measuring at least one of:
   i) a capacitance-related property of the absorptive sensor element, wherein the first member and the second member are conductive, and wherein the detection layer is dielectric;
   ii) at least one spectral feature of reflected light, wherein the first member is reflective, the second member is semi-reflective, and the detection layer is optically transmissive, wherein a portion of the reflected light is reflected by the first member and wherein a portion of the reflected light is reflected by the second member; or
   iii) both i) and ii).

In some embodiments, the first member is disposed on a substrate. In some embodiments, the second member is disposed on a substrate.

In some embodiments, the first member and the second member are conductive, the detection layer is dielectric, and step d) comprises i).

In some embodiments, the first member is reflective, the second member is semi-reflective, and the detection layer is optically transmissive; and step d) comprises ii).

In some embodiments, the absorptive sensor element is heated to a temperature in a range of from 40° C. to 80° C. In some embodiments, the absorptive sensor element is heated to a temperature in a range of from 50° C. to 65° C.

Advantageously, methods according to the present disclosure enable absorptive sensor usage under a wide range of ambient temperatures and have reduced interference from humidity. Moreover, the response time and the purge time between measurements are reduced, and the range of concentrations detectable by the sensors is extended.

As used herein, the term "permeable" in reference to a layer of a material means that in areas where the layer is present, the layer is sufficiently porous to be non-reactively permeable through its thickness (e.g., at 25° C.) by at least one organic compound.

As used herein, the term "capacitance-related property" encompasses any electrical property and the measurement thereof that is in general associated with the imparting of an electrical charge (whether static or time variant) and the monitoring of an electrical property during and/or after the imparting of the charge. Such properties include, for example, not only capacitance, but also impedance, inductance, admittance, current, resistance, conductance, and may be measured according to various methods known in the art.

As used herein, the term "spectral feature" in the context of a reflection spectrum refers to an identifiable feature of the reflection spectrum such as, for example, a peak (a reflection maximum), a valley (reflection minimum), or an inflection point). The size (intensity) and/or wavelength of spectral feature(s) may change in response to the presence of an analyte. Upon a shift in the position or size of one of more peaks (e.g., due to a change in the concentration of an analyte), the amount, spectral distribution, or intensity of reflected light that is detected by the photodetector may change.

Features and advantages of the present disclosure will be further understood upon consideration of the detailed description as well as the appended claims.

BRIEF DESCRIPTION OF THE DRAWINGS

FIG. 1 is a schematic cross-sectional view of an exemplary absorptive sensor element useful in practice of the present disclosure.

DETAILED DESCRIPTION

Methods according to the present disclosure involve analyzing an analyte using an absorptive sensor element while the sensor element is heated to an elevated temperature in a range of from 30 to 100° C.

FIG. 1 shows an exemplary absorptive sensor element 100 that is suitable for practice of methods according to the present disclosure. Absorptive sensor element 100 comprises first member 120, second member 140, and detection layer 130 disposed between and contacting first member 120 and second member 140. In some embodiments, first member 120 is disposed on optional substrate 110a. In some embodiments, second member 140 is disposed on optional substrate 110b.

In some embodiments, the first member and the second member are conductive. In these embodiments, the absorptive sensor element may detect changes in a capacitance-related property due to changes in the dielectric constant caused by analyte vapor absorbed by the PIM.

In some embodiments, the first member is reflective, the second member is semi-reflective, and the detection layer is optically transmissive. In these embodiments, the absorptive sensor element may detect changes in the reflection spectrum (e.g., a wavelength shift of at least one spectral feature) of incident light due to changes in the refractive index of the detection layer caused by analyte vapor absorbed by the PIM.

In some embodiments, the first member and the second member are conductive, the first member is reflective, the second member is semi-reflective, and the detection layer is optically transmissive. In these embodiments, the absorptive sensor element may detect changes in the reflection spectrum (e.g., a wavelength shift of at least one spectral feature) of incident light due to changes in the refractive index of the detection layer, and a change in a capacitance-related property due to a change dielectric constant of the detection layer, both due to analyte vapor absorbed by the PIM.

Detection layer 130 comprises a microporous material. In this context, the terms "microporous" and "microporosity" mean that the material has a significant amount of internal, interconnected pore volume, with the mean pore size (as characterized, for example, by sorption isotherm procedures) being less than about 100 nanometers (nm), typically less than about 10 nm. Such microporosity provides that molecules of organic analyte (if present) will be able to penetrate the internal pore volume of the material and take up residence in the internal pores. The presence of such analyte in the internal pores can alter the dielectric properties of the material such that a change in the dielectric constant (or any other suitable electrical property) can be observed.

In some embodiments, the dielectric microporous material comprises a so-called Polymer of Intrinsic Microporosity (PIM). PIMs are polymeric materials with nanometer-scale pores due to inefficient packing of the polymer chains. For example, in *Chemical Communications*, 2004, (2), pp. 230-231, Budd et al. report a series of intrinsically microporous materials containing dibenzodioxane linkages between rigid and/or contorted monomeric building blocks. Representative members of this family of polymers include those generated by condensation of Component A (e.g., A1, A2, or A3) with Component B (e.g., B1, B2, or B3) as shown in Table 1 according to Scheme 1 (below).

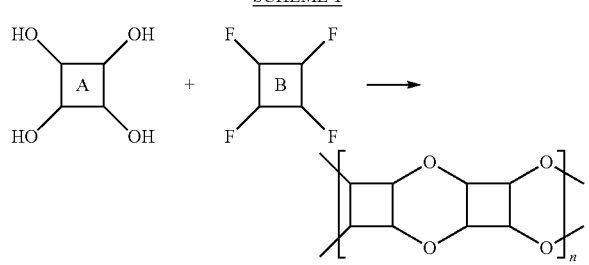

SCHEME 1

TABLE 1

| COMPONENT A | COMPONENT B |
|---|---|
| A1 | B1 |
| A2 | B2 |
| A3 | B3 |

Further suitable Components A and B, and resultant intrinsically microporous polymers, are known in the art, for example, as reported by Budd et al. in *Journal of Materials Chemistry*, 2005, Vol. 15, pp. 1977-1986; by McKeown et al. in *Chemistry, A European Journal*, 2005, Vol. 11, pp. 2610-2620; by Ghanem et al. in *Macromolecules*, 2008, vol. 41, pp. 1640-1646; by Ghanem et al, in *Advanced Materials*, 2008, vol. 20, pp. 2766-2771; by Carta et al. in *Organic Letters*, 2008, vol. 10(13), pp. 2641-2643; in PCT Published Application WO 2005/012397 A2 (McKeown et al.); and in U.S. Patent Appl. Publ. No. 2006/0246273 (McKeown et al.), the disclosure of which is incorporated herein by reference. Such polymers can be synthesized, for example, by a step-growth polymerization where a bis-catechol such as, e.g., A1 (5,5',6,6'-tetrahydroxy-3,3,3',3'-tetramethyl-1,1'-spirobisindane) is allowed to react with a fluorinated arene such as, e.g., B1 (tetrafluoroterephthalonitrile) under basic conditions. Due to the rigidity and contorted nature of the backbone of the resulting polymers, these polymers are unable to pack tightly in the solid state and thus have at least 10 percent free volume and are intrinsically microporous.

PIMs may be blended with other materials. For example, a PIM may be blended with a material that itself is not an absorptive dielectric material. Even though not contributing to an analyte response, such a material may be useful for other reasons. For example, such a material may allow the formation of a PIM-containing layer which has superior mechanical properties and the like. In one embodiment, PIMs may be dissolved in a common solvent with the other material to form a homogeneous solution, which may be cast to form an absorptive dielectric blend layer comprising both the PIM and the other polymer(s). PIMs may also be blended with a material that is an absorptive dielectric material (for example, zeolites, activated carbon, silica gel, hyper-crosslinked polymer networks and the like). Such materials may comprise insoluble materials that are suspended in a solution comprising of a PIMs material. Coating and drying of such a solution/suspension may provide a composite absorptive dielectric layer comprising both the PIM material and the additional absorptive dielectric material.

PIMs are typically soluble in organic solvents such as, for example, tetrahydrofuran and can thus be cast as films from solution (e.g., by spin-coating, dip coating, or bar coating). However, characteristics (accessible thicknesses, optical clarity, and/or appearance) of films made from solutions of these polymers may vary markedly depending on the solvent or solvent system used to cast the film. For example, intrinsically microporous polymers of higher molecular weights may need to be cast from relatively unusual solvents (e.g., cyclohexene oxide, chlorobenzene, or tetrahydropyran) to generate films with desirable properties for use in optochemical sensors as described herein. In addition to solution coating methods, the detection layer may be applied to the either of the first or second members by any other suitable method.

After a PIM is deposited (e.g., coated) or otherwise formed so as to comprise an absorptive dielectric layer, the material may be crosslinked using a suitable crosslinking agent such as, for example, bis(benzonitrile)palladium(II) dichloride. This process may render the absorptive dielectric layer insoluble in organic solvents, and/or may enhance certain physical properties such as durability, abrasion resistance, etc., which may be desirable in certain applications.

PIMs may be hydrophobic so that they will not absorb liquid water to an extent that the material swells significantly or otherwise exhibits a significant change in a physical property. Such hydrophobic properties are useful in providing an organic analyte sensor element that is relatively insensitive to the presence of water. The material may however comprise relatively polar moieties for specific purposes.

The detection layer may comprise a continuous matrix. Such a matrix is defined as an assembly (e.g., a coating, layer, etc.) in which the solid portion of the material is continuously interconnected (irrespective of the presence of porosity as described above, or of the presence of optional additives as discussed below). That is, a continuous matrix is distinguishable from an assembly that comprises an aggregation of particles (e.g., zeolites, activated carbons, carbon nanotubes, etc.). For example, a layer or coating deposited from a solution will typically comprise a continuous matrix (even if the coating itself is applied in a patterned manner and/or comprises particulate additives). A collection of particles deposited via powder spraying, coating and drying of a dispersion (e.g., a latex), or by coating and drying of a sol-gel mixture, may not comprise a continuous network. However, if such a latex, sol-gel, etc., layer can be consolidated such that individual particles are no longer discernible, nor is it possible to discern areas of the assembly that were obtained from different particles, such a layer may then be considered to be a continuous matrix.

Optional substrates 110a or 110b may be a continuous slab, layer, or film of material. If present, it is disposed in sufficient proximity to the first member or the second member that it may serve to provide physical strength and integrity to the absorptive sensor element. Any solid material having structural integrity, flexible or rigid, may be used, subject to type of sensor element. For example, if the sensor element is a capacitance-related property sensor element, then the substrate should generally be dielectric. Suitable dielectric materials may be used, including, for example, glass, ceramic, and/or plastic. In the case of optochemical sensor elements, the design considerations are less stringent. In some embodiments, the substrate has a flat major surface on which the first member is disposed. In large scale production, a polymeric film (such as polyester or polyimide) may be used.

Absorptive sensor element 100 may be, for example, a capacitance-related property sensor element or an optochemical sensor element. These are discussed further below.

Capacitance-Related Property Sensor Element

In one implementation, the absorptive sensor element comprises a capacitance-related property sensor element. In this implementation, the first member and the second member are conductive electrodes, and for simplicity are referred to hereinbelow as the base conductive electrode and the permeable conductive electrode, respectively.

The base conductive electrode can comprise any suitable conductive material. Combinations of different materials (conductive and/or nonconductive) can be used, as different layers or as a mixture, as long as sufficient overall conductivity is provided, Typically, the base conductive electrode has a sheet resistance of less than about $10^7$ ohms/square. Examples of materials that can be used to make the base conductive electrode and/or permeable conductive electrode include, but are not limited to, organic materials, inorganic materials, metals, alloys, and various mixtures and composites comprising any or all of these materials. In certain embodiments, coated (for example, thermal vapor coated, sputter coated, etc.) metals or metal oxides, or combinations thereof, may be used. Suitable conductive materials include for example aluminum, nickel, titanium, tin, indium-tin oxide, gold, silver, platinum, palladium, copper, chromium, and combinations thereof.

The base conductive electrode can be of any thickness as long as it is conductive; for example, it may have a thickness in a range of from at least 4 nm to 1000 nm, or from 10 nm to 200 nm.

In certain embodiments, the base conductive electrode is fabricated such that it follows a tortuous path. This typically serves to increase the area that may be heated and/or increase the rate of heating. In general, the design of the base conductive electrode should allow for facile resistive heating when in electrical communication with the heater circuit element. Such design considerations are within the skill level of one of ordinary skill in the art.

The permeable conductive electrode may include additional components as long as it remains permeable by at least one organic analyte. Examples of materials that can be used to make the permeable conductive electrode include organic materials, inorganic materials, metals, alloys, and various mixtures and composites comprising any or all of these materials. In certain embodiments, coated (for example, thermal vapor coated, or sputter coated) metals or metal oxides, or combinations thereof, may be used. Suitable conductive materials include for example aluminum, nickel, titanium, tin, indium-tin oxide, gold, silver, platinum, palladium, copper, chromium, carbon nanotubes, and combinations thereof. In certain embodiments, the permeable conductive electrode is formed by printing a silver ink, followed by drying the ink. Details concerning vapor-deposited permeable conductive electrodes can also be found in U.S. Provisional Patent Appln. No. 61/388,146 (Palazzotto et al.), the disclosure of which is incorporated herein by reference.

Combinations of different materials (conductive and/or nonconductive) can be used, as different layers or as a mixture, as long as sufficient overall conductivity and permeability is provided. Typically, the permeable conductive electrode has a sheet resistance of less than about $10^7$ ohms/square.

The permeable conductive electrode typically has a thickness in a range of from 1 nm to 100 nm, although other thicknesses may be used. For example, in some embodiments the permeable conductive electrode may have a thickness in a range of from 1 nm to 3000 nm, or even from 40 nm to 200 nm. Greater thicknesses may have undesirably low levels of permeability, while lesser thicknesses may become insufficiently conductive and/or difficult to electrically connect to the second conductive member. Since the permeable conductive electrode is permeable, the base conductive electrode typically comprises a continuous, uninterrupted layer, but it may contain openings or other interruptions if desired. Further details concerning capacitance-related property sensors including a microporous polymer and silver ink-coated permeable conductive electrodes, and methods for their manufacture can be found, for example, in PCT International Publication No. WO 2009/045733 A2 (Gryska et al.).

In this implementation, the physical thickness of the detection layer is desirably in a range of from 150 to 1200 nanometers, for example, in a range of from 500 to 900 nanometers, although thinner and thicker detection layers may also be used.

If desired a side by side arrangement of the first and permeable conductive electrodes may also be used instead of the parallel plate configuration discussed above. Examples of such configurations are discussed in Provisional Patent Appln. No. 61/475,009 entitled "VAPOR SENSOR INCLUDING SENSOR ELEMENT WITH INTEGRAL HEATING", filed concurrently herewith, the disclosure of which is incorporated herein by reference.

Optochemical Sensor Element

In one implementation, the absorptive sensor element comprises an optochemical sensor element. In this implementation, the second member is semi-reflective and the first member is at least partially reflective (desirably highly-reflective), and for simplicity are referred to hereinbelow as the semi-reflective member and reflective member, respectively.

In this implementation, the semi-reflective member and reflective member are typically arranged such that they are parallel to one another. Light that is incident on the semi-reflective member is partially reflected and partially transmitted, whereby it is transmitted to the reflective member, which in turn reflects a portion of the light. In this embodiment, the detection layer is optically transmissive.

The semi-reflective member is permeable by at least one organic analyte and semi-reflective to visible light; that is, it reflects some incident light (e.g., at least 20, 30, 40, or 50 percent) and transmits (e.g., at least 20, 30, 40, or 50 percent) some incident light over a wavelength range of from 300 nm to 2500 nm, typically over a wavelength range of from 300 nm to 1100 nm. Suitable semi-reflective members include, for example, thermal vapor deposited metallic films comprising metals such as copper, silicon, aluminum, rhodium, iridium, nickel, chromium, osmium, gold, silver, palladium, or a combination thereof. In general, the semi-reflective member may have any thickness as long as it remains semi-reflective. Typically, these properties may be achieved at a thickness of from 1 nm to 50 nm, more typically from 1 nm to 10 nm, and even more typically from 4 nm to 10 nm, although other thickness may also be used. Desired thicknesses will typically depend on the material used to form the semi-reflective member, the material onto which the semi-reflective member is deposited, the analyte to be detected, and the medium that will carry the analyte. Details concerning vapor-deposited vapor permeable conductive electrodes, suitable for use as semi-reflective members, can also be found in U.S. Provisional Patent Appln. No. 61/388,146 (Palazzotto et al.), the disclosure of which is incorporated herein by reference.

The reflective member may be made of any material that has a reflective surface. The reflective member may be a unitary body, and may be relatively thick or thin. Examples of unitary bodies include reflective metal foils or sheets. Optionally, the reflective member may comprise a substrate having a reflective layer disposed thereon, wherein the optional substrate is as defined hereinabove. The reflective member material can be tailored to the application. Examples of suitable reflective layers include vapor deposited metals having a thickness of 1 nm to 10 microns, or even from 1 nm to 5 microns, although other thicknesses may also be used. For example, the reflective member may have sufficient thickness to be self-supporting (e.g., in a range of from 10 micrometers to one centimeter), although large and lesser thicknesses may also be used. Exemplary suitable materials for the reflective layer include aluminum, chromium, gold, nickel, titanium, palladium, platinum, silicon, silver, and combinations thereof.

In embodiments wherein reflective member is also semi-reflective, the reflective member desirably reflects at least 20 percent, 30 percent, or even at least 40 percent of at least a portion of light that is incident on it within a wavelength range of from 300 nm to 2500 nm. In embodiments where the reflective member is highly reflective, the reflective member desirably reflects at least 50 percent, 60 percent, 70 percent, 80 percent, or even at least 90 percent, or more of at least a portion of light that is incident on it within a wavelength range of from 300 nm to 2500 nm, although a lesser reflectivity may also be used.

At least one of the reflective member and the semi-reflective member should be permeable to any analyte vapor with which the sensor element is to be used.

For example, referring now to FIG. 1, in one embodiment, first member 120 is reflective and disposed on optional substrate 110a, and second member 140 is semi-reflective and permeable to the analyte vapor. In this configuration, a portion of the incident light is directed onto and through second member 140 and reflected by first member 120.

In another embodiment, first member 120 is reflective and permeable to the analyte vapor. Second member 140 is semi-reflective and is disposed on optional substrate 110b, which is optically transmissive to a portion of the incident light. In this configuration, incident light is directed onto and through optional substrate 110b.

In this implementation, the physical thickness of the detection layer is in a range of from 150 to 1200 nm, for example, in a range of from 500 to 900 nm, although thinner and thicker detection layers may also be used.

Further details concerning optochemical sensors can be found, for example, in U.S. Pat. No. 7,556,774 (Rakow et al.) and U.S. Pat. No. 7,906,233 (Rakow et al.), and in Provisional Patent Appln. No. 61/475,000 entitled "METHOD OF DETECTING VOLATILE ORGANIC COMPOUNDS", filed concurrently herewith, the disclosure of which is incorporated herein by reference.

Effect of Temperature

In practice of methods according to the present disclosure, elevated temperature in a range of from 30° C. to 100° C. is used. Desirably, the temperature is in a range of from between 40° C. to 80° C., or even between 50° C. and 65° C. Insufficient heating may cause slow response and cycle time. Excess heating generally reduces sensitivity of the absorptive sensor element, and may even lead to sensor degradation under some circumstances. However, quite unexpectedly it is presently discovered that while the sensitivity may be reduced, the concentration range of the analyte over which measurements can be made is extended; for example as shown in the following examples.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight. In the Examples, the term "ppm" refers to parts per million, and the term "R.H." refers to relative humidity.

Preparation of PIM A

PIM A was prepared from the monomers 5,5',6,6'-tetrahydroxy-3,3,3',3'-tetramethyl-1,1'-spirobisindane and tetrafluoroterephthalonitrile generally according to the procedure reported by Budd et al. in *Advanced Materials*, 2004, Vol. 16, No. 5, pp. 456-459. 19.31 grams of 5,5',6,6'-tetrahydroxy-3,3,3',3'-tetramethyl-1,1'-spirobisindane were combined with 11.34 g of tetrafluoroterephthalonitrile, 47.02 g potassium carbonate, and 500 milliliters of N,N-dimethylformamide, and the mixture was reacted at 65° C. for 48 hours. The resulting polymer was dissolved in tetrahydrofuran, precipitated three times from methanol, and then dried under vacuum at room temperature. A yellow solid product was obtained having a number-average molecular weight ($M_n$) of approximately 64,300 g/mol, as determined by gel permeation chromatography analysis using light scattering detection.

Preparation of PIM B

PIM B was prepared from the monomers 5,5',6,6'-tetrahydroxy-3,3,3',3'-tetramethyl-1,1'-spirobisindane and tetrafluoroterephthalonitrile generally according to the procedure reported by Budd et al. in *Advanced Materials*, 2004, Vol. 16, No. 5, pp. 456-459. 100 grams of 5,5',6,6'-tetrahydroxy-3,3,3',3'-tetramethyl-1,1'-spirobisindane were combined with 59.22 g of tetrafluoroterephthalonitrile, 243.6 g potassium carbonate, and 2543.6 g of N,N-dimethylformamide, and the mixture was reacted at 65° C. for 72 hours. The resulting polymer was dissolved in tetrahydrofuran, precipitated three times from methanol, and then dried under vacuum at room temperature. A yellow solid product was obtained a number-average molecular weight ($M_n$) of approximately 40,800 g/mol respectively, as determined by gel permeation chromatography analysis using light scattering detection.

Preparation of Sensor Element (Method 1)

Sensor elements were prepared on 2 inches×2 inches (5.1 cm×5.1 cm) Schott glass slides (cut from 440×440 mm panels, 1.1 mm thick, D-263 T Standard glass from Schott North America, Elmsford, N.Y.), which were cleaned by soaking them for 30 to 60 minutes in ALCONOX LIQUI-NOX detergent solution (from Alconox, Inc. of White Plains, N.Y.), then scrubbing each side of the slides with a bristle brush, rinsing them under warm tap water followed by a final rinse with deionized water (DI water). The slides were allowed to air dry covered to prevent dust accumulation on the surface. The dry, clean slides were stored in 7.6 cm wafer carriers obtained from Entegris, Chaska, Minn.

A base conductive electrode was deposited onto the Schott glass slide by e-beam evaporative coating 10.0 nm of titanium at a rate of 0.1 nm per second (nm/sec) followed by 150.0 nm of aluminum (obtained as shot, 4-8 mm, Puratronic grade 99.999% from Alfa Aesar) at 0.5 nm/sec using a 2 inches (5 cm)×2 inches (5 cm) square mask (MASK A) having a single rectangular opening with a top border of 0.46 inch (1.2 cm), a bottom border of 0.59 inch (1.5 cm), and left and right borders of 0.14 inch (0.35 cm) prepared from laser-cut 1.16 mm thick stainless steel. All masks were deburred before using to minimize the possibility of shorts caused by sharp edges in the mask. The vapor deposition process was controlled using an INFICON XTC/2 THIN FILM DEPOSITION CONTROLLER from INFICON of East Syracuse, N.Y.

A solution of the PIM material in chlorobenzene was prepared by mixing the components in a small jar, and placing it on a roller mill (available as MINI BOTTLE ROLLER, number 348920, from Wheaton Science Products, Millville, N.J.) overnight, then filtering through a one-micron ACRODISC filter (obtained as ACRODISC 25 MM SYRINGE FILTER WITH 1 MICRON GLASS FIBER MEMBRANE from PALL Life Sciences of Ann Arbor, Mich.). The solution was allowed to sit overnight so that any bubbles that formed could escape.

The base conductive electrode was cleaned by placing a specimen (i.e., glass slide with conductive electrode thereon), in a WS-400B-8NPP-LITE SINGLE WAFER spin processor manufactured by Laurell Technologies, Corp. North Wales, Pa., and placing about 0.5 mL of chlorobenzene on the base conductive electrode, then running through a spin coating cycle of 1000 rpm for 1 minute.

The solution of PIM material was then coated onto the base conductive electrode under the same spin coating conditions.

After spin-coating, PIMs thickness measurements were made using a Model XP-1 PROFILOMETER from AMBiOS Technology of Santa Cruz, Calif. by removing a small section of the coating with an acetone soaked cotton swab. The parameters used in the thickness measurement were a scan speed of 0.1 mm/sec, a scan length of 5 mm, a range of 10 micrometers, a stylus force of 0.20 mg and a filter level of 4. All specimens were baked for 1 hour at 100° C. after coating.

A patterned second, silver, conductive electrode was inkjet printed on top of the PIM material according to a pattern that produced a 2×2 array of four 0.60 inch (1.5 cm) height×0.33 inch (0.84 cm) width rectangular ink patches vertically separated by 0.22 inch (0.56 cm) and horizontally separated by 0.48 inch (1.2 cm). In order to inkjet print the permeable conductive electrode, a bitmap image (702 dots per inch) was created and downloaded to an XY deposition system. The printhead used for depositing a silver nanoparticle sol was a DIMATIX SX3-128 printhead (FUJIFILM Dimatix, Santa Clara, Calif.) with a 10 pL drop volume and 128 jets/orifices, the printhead assembly being approximately 6.5 cm long with 508 micron jet to jet spacing. The silver nanoparticle sol used to construct this electrode was obtained from Cabot Corp., Boston, Mass., under the designation AG-IJ-G-100-S1. The silver nanoparticle sol was approximately 15-40 percent by weight ethanol, 15-40 percent by weight ethylene glycol, and 20 percent by weight silver. The specimen was held securely during the inkjet printing process by use of a porous aluminum vacuum platen. Upon completion of printing, the specimen was removed from the porous aluminum vacuum platen and placed on a hot plate for 15 minutes at 125° C.

After depositing the second conducting electrode, a connecting electrode was prepared by using DGP-40LT-25C silver nanoparticle ink from ANP, 244 Buyong industrial complex, Kumho-ri, Buyong-myeon, Chungwon-kun, Chungcheongbuk-do, South Korea. A small artist brush was used to paint a connection to the permeable conductive electrode to facilitate electrical contact for testing. After painting this connection, the sensors were baked for one hour at 150° C. to set the ink.

This sensor production process produced a set of 4 sensor elements of approximately 8 mm×10 mm active area (area under the overlapping base conductive electrode and the permeable conductive electrodes that was not covered by the connecting electrode) on an approximately 50 mm×50 mm glass substrate. Individual sensor elements were produced by dicing the specimen using a standard glass scoring cutter on the back (inactive side) while supporting the sensor elements so that their front (active) surfaces would not be damaged. After dicing into individual sensor elements, the sensors were stored in 3.81 cm wafer holders from Entegris of Chaska, Minn.

Preparation of Sensor Element (Method 2)

Sensor elements were prepared on PGO glass slides (glass number 0050-0050-0010-GF-CA, 50 mm×50 mm, 1.1 mm thick, material C-263, surface 80/50, obtained from Precision Glass & Optics of Santa Ana, Calif.), which were cleaned by soaking them for 30 to 60 minutes in ALCONOX LIQUI-NOX detergent solution, then scrubbing each side of the slides with a bristle brush, rinsing them under warm tap water followed by a final rinse with deionized water (DI water). The slides were allowed to air dry covered to prevent dust accumulation on the surface. The dry, clean slides were stored in 7.6 cm (3 inch) wafer carriers obtained from Entegris of Chaska, Minn.

A base conductive electrode was deposited onto the PGO glass slide by thermally vapor coating 5.0 nm (nm) of titanium (obtained as titanium slug, 9.5 mm×9.5 mm, 99.9+% purity from Alfa Aesar, Ward Hill, Mass.) at a rate of 0.1 nm per second (nm/sec) followed by 100.0 nm of nickel (obtained as 99.995% pure from Alfa Aesar) at 0.1 nm/sec or 150 nm of aluminum (obtained as Puratonic grad 99.999% from Alfa Aesar) at 0.1 nm/sec using a 2 inches (5 cm)×2 inches (5 cm) square mask (MASK A) having a single rectangular opening with a top border of 0.46 inch (1.2 cm), a bottom border of 0.59 inch (1.5 cm), and left and right borders of 0.14 inch (0.35 cm) prepared from laser-cut 50 gauge stainless steel. The deposition process was controlled using an INFICON XTC/2 THIN FILM DEPOSITION CONTROLLER from INFICON of East Syracuse, N.Y.

A solution of PIM material in chlorobenzene was prepared by mixing the components in a small jar, and placing it on a roller mill overnight or until the polymer was substantially dissolved, then filtering through a one-micron ACRODISC filter. The solution was allowed to sit overnight so that any bubbles that formed could escape. The base conductive electrode was cleaned by placing a specimen (i.e., glass slide with conductive electrode thereon), in a WS-400B-8NPP-LITE SINGLE WAFER spin processor manufactured by Laurell Technologies, Corp. North Wales, Pa., and placing about 0.5 mL of chlorobenzene on the base conductive electrode, then running through a spin coating cycle of 1000 rpm for 1 minute.

For each specimen, a solution of PIM material was then coated onto the base conductive electrode under the same spin coating conditions. After spin-coating, PIMS thickness measurements were made using a Model XP-1 PROFILOMETER (from AMBiOS Technology of Santa Cruz, Calif.) by removing a small section of the coating with an acetone soaked cotton swab. The parameters used in the thickness measurement were a scan speed of 0.1 mm/sec, a scan length of 5 mm, a range of 10 micrometers, a stylus force of 0.20 mg and a filter level of 4. All specimens were baked for 1 hour at 100° C. after coating. A 2 inches (5 cm)×2 inches (5 cm) mask (MASK B) having a 2×2 regular array of four 0.60 inch (1.5 cm) height×0.33 inch (0.84 cm) width rectangular openings vertically separated by 0.22 inch (0.56 cm) and horizontally separated by 0.48 inch (1.2 cm) was made from 24 gauge stainless steel by laser milling. A permeable conductive electrode was vapor deposited through MASK B using thermal deposition of gold (obtained as metal spatters, 99.999% typical purity from Cerac Inc., Milwaukee, Wis.) at various thicknesses. A deposition rate of 0.1 nm/sec was used for 6 nm. After depositing the permeable conductive electrode (to facilitate electrical contact for testing), a connecting electrode was deposited by thermally vapor coating 10.0 nm of titanium (obtained as titanium slug, 9.5 mm×9.5 mm, 99.9+% purity from Alfa Aesar) at a rate of 0.1 nm/sec followed by 100 nm of nickel or 150.0 nm of aluminum at 0.5 nm/sec through a 2 inches (5 cm)×2 inches (5 cm) mask (MASK C) having two horizontal rectangular openings with a height of 0.4 inch (1 cm), left and right borders of 0.14 inch (0.36 cm), and a separation of 0.92 inch (2.4 cm), prepared by laser milling from 50 gauge stainless. The deposition process was controlled using an INFICON XTC/2 THIN FILM DEPOSITION CONTROLLER.

This sensor production process produced an element of approximately 10 mm×9 mm active area (area under the overlapping base conductive electrode and the permeable conductive electrodes that was not covered by the connecting electrode) on an approximately 25 mm×25 mm glass substrate.

Capacitance Measurement

All tests were performed in air that had been passed over DRIERITE desiccant to remove moisture, and passed over activated carbon to eliminate any organic contaminates.

The testing chamber allowed the measurement of four sensor specimens at a time. Vapor tests were conducted using a 10 L/minute dry air flow through the system. Various vapor levels were generated using a KD Scientific syringe pump (available from KD Scientific Inc. of Holliston, Mass.) fitted with a 500 microliter gas tight syringe (obtained from Hamilton Company of Reno, Nev.). The syringe pump delivered the organic liquid onto a piece of filter paper suspended in a 500-mL three-necked flask. The flow of dry air pass the paper vaporized the solvent. Delivering the solvent at different rates by controlling the syringe pump generated different concentrations of vapor. The syringe pump was controlled by a LABVIEW (software available from National Instruments of Austin, Tex.) program that allowed vapor profiles to be generated during a test run. A MIRAN IR analyzer (available from Thermo Fischer Scientific, Inc. of Waltham, Mass.) was used to verify the set concentrations. The capacitance and dissipation factors were measured with an Agilent LCR meter (available under the designation Agilent Model E4980A LCR meter from Agilent Technologies. Santa Clara, Calif.) or Instek LCR meter (available under the designation Model 821 LCR meter from Instek America, Corp. Chino, Calif.) applying one volt at 1000 Hz across the base conductive electrode and the permeable conductive electrodes.

Optoelectronic Measurement

The interference reflection spectra were taken using an Ocean Optics spectroscopy system (available from Ocean Optics, Model Jaz). The Ocean Optics reflection optical probe was located above 10 mm×9 mm active area of the capacitor configuration. A spectrum from a silver mirror was used for a reference spectrum for reflection intensity. The wavelength range of reflection spectra was from 340.58 nm to 1031.1 nm. The valley positions of spectra were obtained using a customized LABVIEW program after testing. The wavelength shift of reflection spectrum valley positions around 850 nm were measured.

Humidity Control

For humidity control experiments, the humidity was generated by passing dry air flow over a 500 mL temperature controlled water jacketed flask. The air stream of dry air was regulated by a Matheson gas flow meter and the flow rate of air was 10 L/min. Around 250 mL of distilled water was contained in the flask and dry air was delivered to evaporate water. Proper humidity was generated by controlling the temperature of circulating water which was connected to a Heating/Cooling Circulator (available from VWR, Model 11605). Then, the humid air was delivered to the vapor generating flask described above. Polytetrafluoroethylene (PTFE) tubing was used throughout the delivery system. The humidity and temperature was monitored and recorded with an iTHX-M Humidity Meter (available from Omega Engineering Inc. of Stamford, Conn.).

Temperature Control

The temperature of sensor elements was controlled using flexible heaters, thermocouples, and a feedback-loop controlling program. The flexible heaters (available from Omega Engineering, Inc) were located underneath aluminum plates and thermocouples were located between aluminum plates and flexible heaters. The sensors were placed on the aluminum plates. The actual temperature of the sensor elements was calibrated using thermocouples on the sensor elements and thermocouples under the aluminum plates. The heaters were connected to 24V DC power supply and switches. The temperature of heaters was controlled by a customized LABVIEW program. Two different temperatures will be described. One is the sensor element temperature which is the actual temperature of sensor using the temperature controller and the other one is the surrounding temperature which is measured at ambient temperature during the experiments.

Example 1

Sensor Element 1 was made by METHOD 1 using PIM B as a 4.5 percent by weight solution in chlorobenzene. The thickness of PIM layer was 479 nm. The response time of the sensor element, $t_{90}$, is defined as the time required for the sensor element to register 90 percent of the total change in response from a first vapor concentration to a second, different, vapor concentration.

For example, when methyl ethyl ketone (MEK) concentration was changed from 50 to 100 ppm, the capacitance $C_{90}$ is defined as $C_{90}$=((maximum capacitance at 100 ppm MEK−maximum capacitance at 50 ppm MEK)*0.9)+maximum capacitance at 50 ppm MEK The quantity, $t_{90}$ is equal to the first time after the MEK concentration was changed from 50 ppm to 100 ppm when the capacitance reached the value of $C_{90}$. The response time of the sensor element, $t_{90}$, for the valley position was calculated by an analogous method.

Sensor Element 1 was exposed to various solvents at various concentrations at various sensor element temperatures. The capacitance values of the sensor element were measured. The surrounding temperature was 25° C. Results using Example 1 are reported in Table 2 (below).

TABLE 2

| ANALYTE VAPOR | SENSOR ELEMENT TEMPERATURE, ° C. | $t_{90}$, sec |
|---|---|---|
| MEK | 25 | 338 |
| (0 ppm to 50 ppm) | 55 | 105 |
| MEK | 25 | 122 |
| (50 ppm to 100 ppm) | 55 | 86 |
| Toluene | 35 | 383 |
| (0 ppm to 12 ppm) | 40 | 340 |
|  | 45 | 307 |
|  | 55 | 252 |
| Toluene | 35 | 287 |
| (12 ppm to 25 ppm) | 40 | 224 |
|  | 45 | 215 |
|  | 55 | 130 |

Example 2

Sensor Element 2 was made by METHOD 2 using PIM A as a 5.5 percent by weight solution in chlorobenzene, and using aluminum for the base conductive electrode and the connecting electrodes. The thickness of PIM layer was 783 nm. Example 2 was exposed to average 125 ppm of isopropanol for 30 min daily and was kept in a humidity chamber (Relative Humidity=95 percent, 22° C.) for 21 days. After 21 days in the humidity chamber, Example 2 was exposed to isopropanol at various concentrations and various sensor element temperatures. The surrounding temperature was 23° C. Results of capacitance measurements are reported in Table 3 (below).

TABLE 3

| ANALYTE VAPOR | SENSOR ELEMENT TEMPERATURE, ° C. | $t_{90}$, sec |
|---|---|---|
| Isopropanol | 23 | 385 |
| (0 ppm to 50 ppm) | 55 | 108 |
| Isopropanol | 23 | 346 |
| (50 ppm to 200 ppm) | 55 | 164 |

Example 3

Example 3 was made by METHOD 2 using PIM B as a 4 percent by weight solution in chlorobenzene, and using nickel for the base conductive electrode and the connecting electrodes. The thickness of PIM layer was 745 nm. Example 3 was exposed to octane at various concentrations and various sensor element temperatures. The valley positions of reflection spectra around the wavelength of 850 nm were measured. The surrounding temperature was 23° C. Results using Example 3 are reported in Table 4 (below).

TABLE 4

| ANALYTE VAPOR | SENSOR ELEMENT TEMPERATURE, ° C. | $t_{90}$, sec |
|---|---|---|
| Octane | 23 | 491 |
| (50 ppm to 100 ppm) | 55 | 221 |
| Octane | 23 | 551 |
| (100 ppm to 200 ppm) | 55 | 242 |
| Octane | 23 | 641 |
| (200 ppm to 300 ppm) | 55 | 303 |

Example 4

Sensor Element 4 was made by METHOD 2 using PIM B as a 4 percent by weight solution in chlorobenzene, and using nickel for the base conductive electrode and the connecting electrodes. The thickness of PIM layer was 745 nm. Sensor Element 4 was exposed to a series of toluene concentrations under dry air (0% relative humidity (R.H.)) at two different sensor element temperatures (23° C. and 55° C.). The surrounding temperature was 23° C. The capacitance values of the sensor element were measured. Results using Sensor Element 4 are reported in Table 5 (below).

TABLE 5

| TOLUENE CONCENTRATION, ppm | CAPACITANCE at 23° C. and 0% R.H., pF | CAPACITANCE at 55° C. and 0% R.H., pF |
|---|---|---|
| 0 | 2542 | 2529 |
| 3 | 2644 | 2550 |
| 6 | 2655 | 2566 |
| 12 | 2671 | 2580 |
| 25 | 2681 | 2600 |
| 50 | 2683 | 2620 |
| 100 | 2678 | 2639 |
| 200 | 2658 | 2653 |

Example 5

Sensor Element 5 was made by METHOD 2 using PIM B as a 4 percent by weight solution in chlorobenzene, and using nickel for the base conductive electrode and the connecting electrodes. The thickness of PIM layer was 745 nm. Sensor Element 5 was exposed to a series of octane concentrations under dry air (R.H, 0%) at two different sensor element temperatures (24° C. and 55° C.). The surrounding temperature was 24° C. Valley positions of reflection spectra were measured. Results using Sensor Element 5 are reported in Table 6 (below).

TABLE 6

| OCTANE CONCENTRATION ppm | VALLEY POSITION at 24° C. and 0% R.H., nm | VALLEY POSITION at 55° C. and 0% R.H., nm |
|---|---|---|
| 0 | 836.51 | 844.09 |
| 3 | 861.82 | 854.33 |
| 6 | 867.05 | 858.11 |
| 12 | 871.93 | 861.76 |
| 25 | 878.09 | 866.23 |
| 50 | 884.85 | 870.71 |
| 100 | 893.70 | 876.13 |
| 200 | 905.30 | 882.29 |
| 300 | 913.94 | 886.48 |

Example 6

Sensor Element 6 was made by sensor element preparation METHOD 1 using PIM B as a 4 percent by weight solution in chlorobenzene. The thickness of PIMs layer was 702 nm. Sensor Element 6 was exposed to a series of toluene concentrations under humid air (80% R.H. at 23° C.) at two different sensor element temperatures (23° C. and 55° C.). The surrounding temperature was 23° C. The capacitance values of the sensor element were measured. Results using Sensor Element 5 are reported in Table 7 (below).

TABLE 7

| TOLUENE CONCENTRATION, ppm | CAPACITANCE at 23° C. and 80% R.H., pF |
|---|---|
| 0 | 1206 |
| 3 | 1189 |
| 25 | 1111 |
| 100 | 966 |

| | CAPACITANCE, at 55° C. and 80% R.H., pF |
|---|---|
| 0 | 825 |
| 12 | 858 |
| 25 | 862 |
| 50 | 868 |
| 100 | 873 |
| 200 | 876 |

Select Embodiments of the Present Disclosure

In a first embodiment, the present disclosure provides a method of using an absorptive sensor element, the method comprising the steps:

a) providing the absorptive sensor element, wherein the absorptive sensor element comprises: a first member, a second member, and a detection layer comprising a polymer of intrinsic microporosity disposed between and contacting the first member and the second member;

b) heating the absorptive sensor element to a temperature in a range of from 30° C. to 100° C.;

c) exposing the absorptive sensor element to an analyte vapor, while the absorptive sensor element is at the elevated temperature; and d) measuring at least one of:
  i) a capacitance-related property of the absorptive sensor element, wherein the first member and the second member are conductive, and wherein the detection layer is dielectric;
  ii) at least one spectral feature of reflected light, wherein the first member is reflective, the second member is semi-reflective, and the detection layer is optically transmissive, wherein a portion of the reflected light is reflected by the first member and wherein a portion of the reflected light is reflected by the second member; or
  iii) both i) and ii).

In a second embodiment, the present disclosure provides a method according to the first embodiment, wherein the first member is supported on a substrate.

In a third embodiment, the present disclosure provides a method according to the first embodiment, wherein the second member is supported on a substrate.

In a fourth embodiment, the present disclosure provides a method according to any one of the first to third embodiments, wherein step d) comprises i).

In a fifth embodiment, the present disclosure provides a method according to any one of the first to fourth embodiments, wherein step d) comprises ii).

In a sixth embodiment, the present disclosure provides a method according to any one of the first to fifth embodiments, wherein the absorptive sensor element is heated to a temperature in a range of from 40° C. to 80° C.

In a seventh embodiment, the present disclosure provides a method according to any one of the first to sixth embodiments, wherein the absorptive sensor element is heated to a temperature in a range of from 50° C. to 65° C.

Various modifications and alterations of this disclosure may be made by those skilled in the art without departing from the scope and spirit of this disclosure, and it should be understood that this disclosure is not to be unduly limited to the illustrative embodiments set forth herein.

What is claimed is:

1. A method of using an absorptive sensor element, the method comprising the steps:
    a) providing the absorptive sensor element, wherein the absorptive sensor element comprises: a first member, a second member, and a detection layer comprising a polymer of intrinsic microporosity disposed between and contacting the first member and the second member;
    b) heating the absorptive sensor element to an elevated temperature in a range of from 30° C. to 100° C.;
    while the absorptive sensor element is at the elevated temperature, performing step c) and d):
    c) exposing the absorptive sensor element to an analyte vapor; and
    d) measuring at least one of:
        i) a capacitance-related property of the absorptive sensor element, wherein the first member and the second member are conductive, and wherein the detection layer is dielectric;
        ii) at least one spectral feature of reflected light, wherein the first member is reflective, the second member is semi-reflective, and the detection layer is optically transmissive, wherein a portion of the reflected light is reflected by the first member and wherein a portion of the reflected light is reflected by the second member; or
        iii) both i) and ii).

2. A method according to claim 1, wherein the first member is supported on a substrate.

3. A method according to claim 1, wherein the second member is supported on a substrate.

4. A method according to claim 1, wherein step d) comprises i).

5. A method according to claim 1, wherein step d) comprises ii).

6. A method according to claim 1, wherein the elevated temperature is in a range of from 40° C. to 80° C.

7. A method according to claim 1, wherein the elevated temperature is in a range of from 50° C. to 65° C.

8. A method according to claim 1, wherein step d) comprises measuring iii).

* * * * *